[19] United States Patent
Umeda et al.

(10) Patent No.: US 10,532,191 B2
(45) Date of Patent: Jan. 14, 2020

(54) CATHETER

(71) Applicant: TERUMO KABUSHIKI KAISHA, Shibuya-ku, Tokyo (JP)

(72) Inventors: Yasuhito Umeda, Fujinomiya (JP); Naoyuki Maeda, Odawara (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 229 days.

(21) Appl. No.: 15/437,532

(22) Filed: Feb. 21, 2017

(65) Prior Publication Data

US 2017/0157368 A1 Jun. 8, 2017

Related U.S. Application Data

(63) Continuation of application No. PCT/JP2015/074624, filed on Aug. 31, 2015.

(30) Foreign Application Priority Data

Sep. 4, 2014 (JP) ................. 2014-180079

(51) Int. Cl.
*A61M 25/10* (2013.01)

(52) U.S. Cl.
CPC ........ *A61M 25/10* (2013.01); *A61M 25/1029* (2013.01); *A61M 25/1034* (2013.01); *A61M 2025/1075* (2013.01)

(58) Field of Classification Search
CPC .............. A61M 25/10; A61M 25/1029; A61M 25/1034; A61M 2025/1084; A61M 2025/1075
See application file for complete search history.

(56) References Cited

U.S. PATENT DOCUMENTS

2008/0033477 A1* 2/2008 Campbell ............. A61L 29/085
606/194
2011/0082489 A1 4/2011 Davies, Jr. et al.
2013/0261547 A1 10/2013 Aggerholm et al.

FOREIGN PATENT DOCUMENTS

JP 2008-501408 A 1/2008
JP 2008-253800 A 10/2008
(Continued)

OTHER PUBLICATIONS

BesTech, Modulus of Elasticity—Young Modulus for some common Materials, p. 2, published 2016, available on line Mar. 7, 2019 at https://www.bestech.com.au/wp-content/uploads/Modulus-of-Elasticity.pdf.*

(Continued)

*Primary Examiner* — Amber R Stiles
(74) *Attorney, Agent, or Firm* — Buchanan Ingersoll & Rooney PC

(57) ABSTRACT

A catheter includes a balloon that has an inner layer and an outer layer having elastic stretching properties, having tubular shapes, and being able to be inflated and deflated in response to a change of internal pressure; and a tubular net-shaped reinforcement member that is disposed between the inner layer and the outer layer such that at least a part thereof is movable with respect to the balloon. The reinforcement member has a first sleeve, and second sleeves which respectively surround both end portions of the first sleeve in an axial direction. A maximally inflated diameter of the second sleeve is set so as to be smaller than a maximally inflated diameter of the first sleeve.

14 Claims, 12 Drawing Sheets

(56) References Cited

FOREIGN PATENT DOCUMENTS

| | | |
|---|---|---|
| JP | 2014-518739 A | 8/2014 |
| WO | WO 1996-040350 A1 | 12/1996 |
| WO | 01/64278 A1 | 9/2001 |
| WO | WO 2005/120622 A2 | 12/2005 |
| WO | WO 2014-167220 A1 | 12/2012 |
| WO | 2013/009740 A1 | 1/2013 |

OTHER PUBLICATIONS

The extended European Search Report dated Mar. 19, 2018, by the European Patent Office in corresponding European Patent Application No. 15837668.1-1132. (5 pages).

International Search Report (PCT/ISA/210) dated Nov. 24, 2015, by the Japanese Patent Office as the International Searching Authority for International Application No. PCT/JP2015/074624.

Written Opinion (PCT/ISA/237) dated Nov. 24, 2015, by the Japanese Patent Office as the International Searching Authority for International Application No. PCT/JP2015/074624.

\* cited by examiner

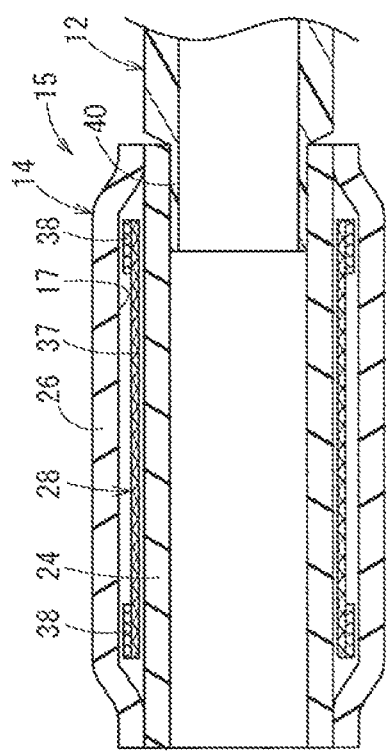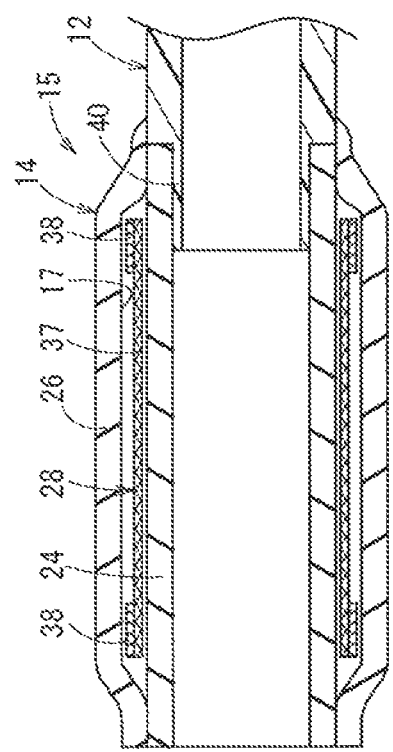

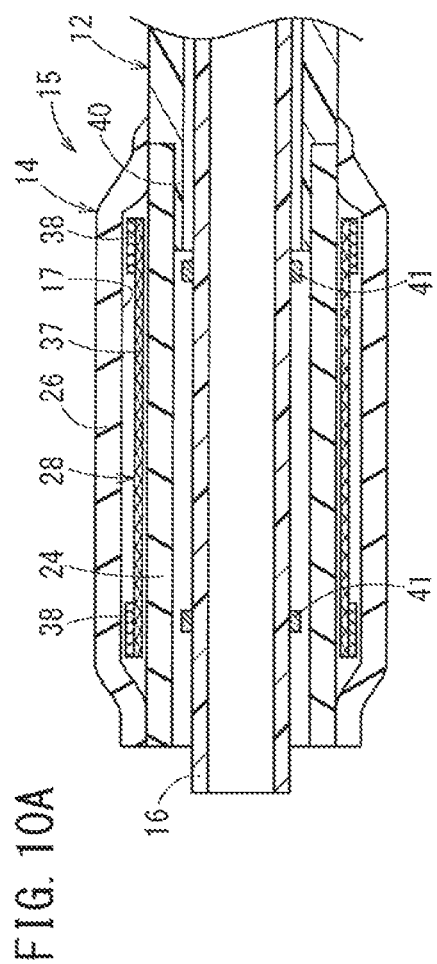
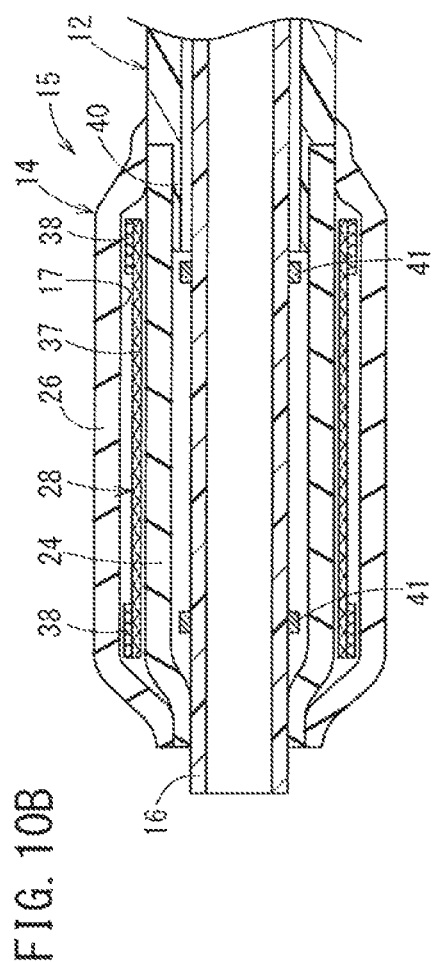
FIG. 10A
FIG. 10B

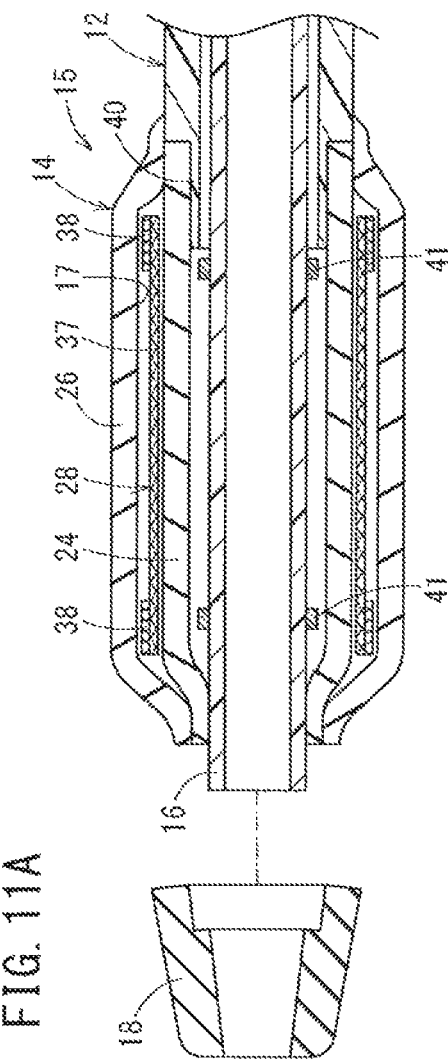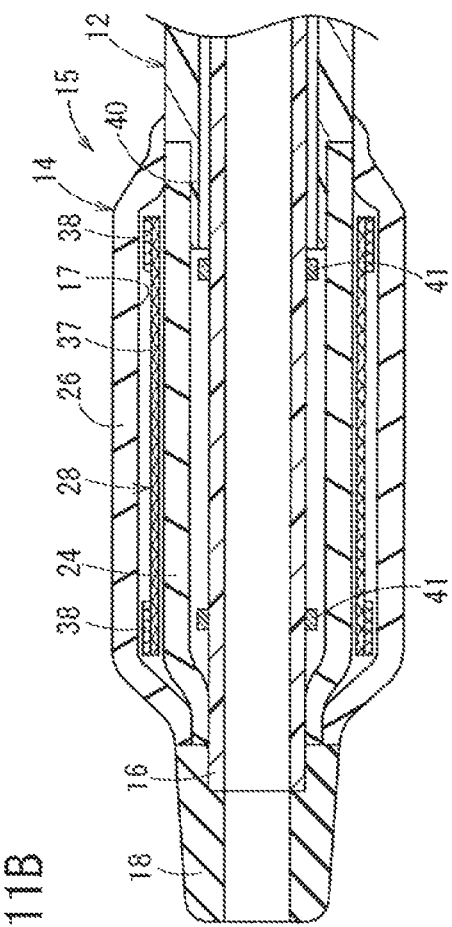

CATHETER

CROSS-REFERENCES TO RELATED APPLICATIONS

This application is a continuation of International Application No. PCT/JP2015/074624 filed on Aug. 31, 2015, which claims priority to Japanese Application No. 2014-180079 filed on Sep. 4, 2014, the entire content of both being incorporated herein by reference.

TECHNICAL FIELD

The disclosure herein relates to a catheter including a balloon reinforced with a reinforcement member.

BACKGROUND DISCUSSION

Recently, in the treatment of acute myocardial infarction and angina pectoris, percutaneous coronary intervention (percutaneous transluminal coronary angioplasty) has been performed such that blood flow is improved by widening a lesion (stenosed portion) of the coronary artery with a balloon catheter (for example, refer to JP-T-2008-501408). Treatment using a balloon catheter has also been performed so as to improve a lesion formed inside other blood vessels, the bile duct, the trachea, the esophagus, the urethra, and other body lumens.

Generally, a balloon catheter is configured to include a long shaft, and a balloon which is provided on the distal side of the shaft and inflates in the radial direction. The balloon catheter is delivered to a stenosed portion in a body after a preceding guide wire is inserted through. In a state where the balloon is disposed at the target stenosed portion, the balloon is inflated by pressure-feeding an inflation fluid into the balloon, and thus, the stenosed portion can be widened.

In order to effectively treat a lesion, the balloon used in the balloon catheter is required to have sufficient strength so as to have a desired balloon shape when being maximally inflated, and to widen the lesion. Therefore, in order to apply high-pressure resistance, low compliance properties, and the like to a balloon, it is known to have a net-shaped reinforcement member in a wall forming the balloon (for example, refer to JP-T-2008-501408).

A balloon catheter can be used to transport a balloon to a lesion inside a body lumen. Since the balloon needs to pass through the inside of the bent body lumen while being transported, the balloon is required to have flexibility so as to follow the bending of the body lumen. However, the technology in the known art, in which a reinforcement member is provided in a wall forming a balloon, is problematic in that the reinforcement member is integrally fixed to the balloon and the degree of freedom of movement with respect to the wall of the balloon is restricted. Hence, it is difficult to achieve sufficient flexibility in the balloon.

SUMMARY

The disclosure herein is directed to a catheter in which flexibility of a balloon reinforced with a reinforcement member can be improved.

According to the disclosure, there is provided a catheter including a balloon that has an inner layer and an outer layer having elastic stretching properties, having tubular shapes, and being able to be inflated and deflated in response to a change of internal pressure; and a tubular net-shaped reinforcement member that is disposed between the inner layer and the outer layer such that at least a part thereof is movable with respect to the balloon. The reinforcement member has a first sleeve, and second sleeves which respectively surround both end portions of the first sleeve in an axial direction. A maximally inflated diameter of the second sleeve is set to be smaller than a maximally inflated diameter of the first sleeve.

According to the disclosure herein, high-pressure resistance and low compliance properties can be applied to the balloon due to the reinforcement member. As used here, the term low compliance properties denotes characteristics in which when the balloon is inflated under high pressure, the balloon diameter is prevented from being excessively widened such that appropriate inflation can be performed. In addition, the reinforcement member has the degree of freedom for moving with respect to the balloon. Therefore, favorable flexibility of the balloon can be maintained.

Hence, in the catheter when the balloon is deflated, high crossability can be realized even inside a complicatedly meandering body lumen. That is, crossability refers to ability of the balloon to pass through the complicatedly meandering body lumen. In addition, when the balloon is inflated, in the reinforcement member, both the end portions of the first sleeve are inflated up to only the maximally inflated diameter of the second sleeve, and other portions of the first sleeve (intermediate portion) are inflated so as to be greater than the second sleeve. Thus, inside a body lumen, the balloon can be inflated so as to have a desired shape, and a procedure can be effectively performed with respect to a lesion.

According to another aspect of the disclosure, a friction coefficient of the second sleeve of the reinforcement member may be greater than a friction coefficient of the first sleeve of the reinforcement member, with respect to the inner layer or the outer layer of the balloon. As such, the reinforcement member can be restrained from causing significant positional misalignment between the inner layer and the outer layer of the balloon in the axial direction from an initial position. In addition, when the friction coefficient between the first sleeve and the second sleeve is increased, the degree of freedom of mutual movement between the first sleeve and the second sleeve is degraded. Therefore, the second sleeve can more effectively conduct a function of restricting inflation.

In a further aspect of the catheter, each of the first sleeve and the second sleeve may be formed by weaving multiple wire members together in an intersecting manner. Since a weaving angle of the wire member configuring the second sleeve may be greater than a weaving angle of the wire member configuring the first sleeve, the maximally inflated diameter of the second sleeve may be set so as to be smaller than the maximally inflated diameter of the first sleeve. When the balloon is inflated, the wire members in each of the first sleeve and the second sleeve are inflated to the critical angle. In this case, due to the difference between the weaving angles of the first sleeve and the second sleeve, an inflating amount of the second sleeve is smaller than an inflating amount of the first sleeve. Therefore, both the end portions of the first sleeve surrounded by the second sleeves are inflated up to only the maximally inflated diameter of the second sleeve. Thus, it is possible to simply establish a configuration in which the intermediate portion of the first sleeve is inflated so as to be greater than both the end portions of the first sleeve surrounded by the second sleeves.

In another aspect of the catheter, the reinforcement member may be formed of high-strength fibers of which tensile break strength is equal to or greater than 2 GPa and an elastic modulus is equal to or greater than 50 GPa. According to this configuration, high-pressure resistance and low compliance properties can be more effectively applied to the balloon.

Thus, according to the disclosure here, in the catheter, flexibility of the balloon reinforced with the reinforcement member can be improved.

BRIEF DESCRIPTION OF THE DRAWINGS

FIG. 9A is a first view describing a step of joining the distal end of a shaft and the proximal end of a balloon to each other, and FIG. 9B is a second view further describing the step of joining the distal end of the shaft and the proximal end of the balloon to each other.

FIG. 10A is a first view describing a step of joining an inner tube and the distal end of the balloon to each other, and FIG. 10B is a second view further describing the step of joining the inner tube and the distal end of the balloon to each other.

FIG. 11A is a first view describing a step of joining a distal tip and the inner tube to each other, and FIG. 11B is a second view further describing the step of joining the distal tip and the inner tube to each other.

DETAILED DESCRIPTION

Hereinafter, a catheter according to the present invention will be described based on a preferable embodiment with reference to the accompanying drawings.

Figure 1:
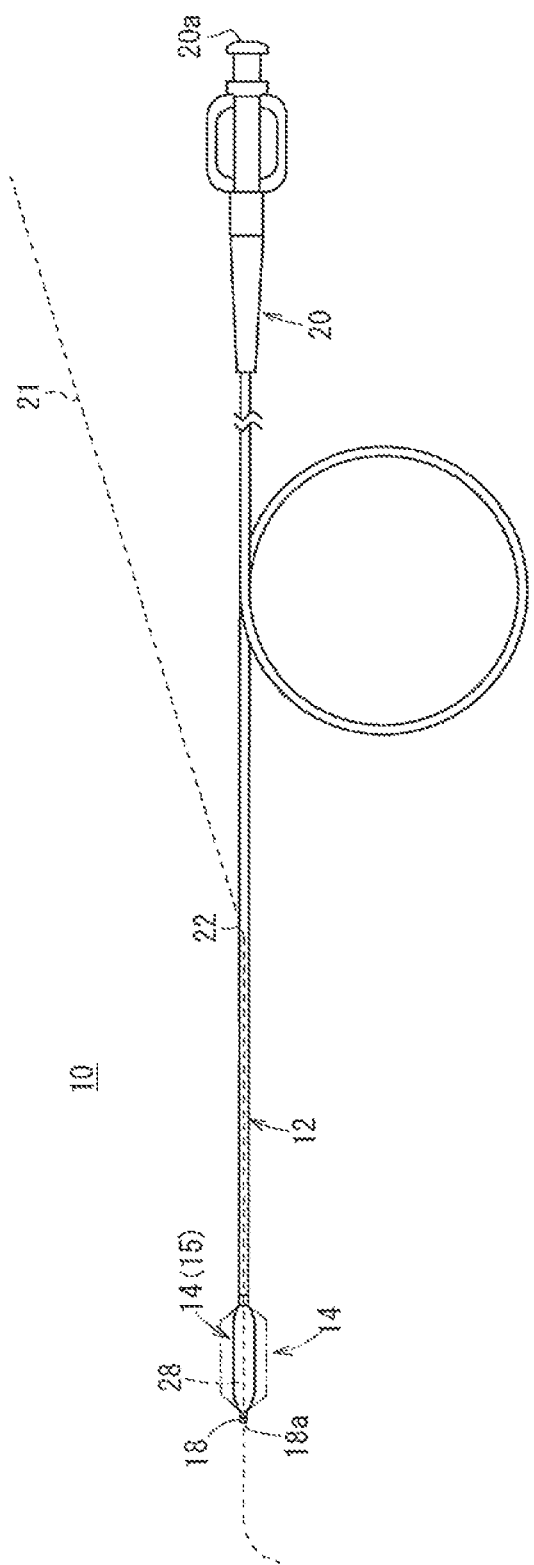
FIG. 1 is a partially-omitted schematic view of a catheter according to an exemplary embodiment of the disclosure.

FIG. 1 is a partially-omitted schematic view illustrating a configuration of a catheter 10, according to an exemplary embodiment of the disclosure herein. The catheter 10 is a so-called PTCA (percutaneous transluminal coronary angio-plasty: percutaneous coronary intervention) inflation catheter for performing treatment in which a long shaft 12 is inserted through a biological organ, for example, the coronary artery, a balloon 14 provided on the distal side thereof is inflated at a stenosed portion (lesion), and the stenosed portion is widened.

The disclosure here can also be applied to a catheter other than the PTCA inflation catheter, for example, a catheter for improving a lesion formed inside biological organs such as other blood vessels, the bile duct, the trachea, the esophagus, the urethra, and other internal organs.

Figure 2:
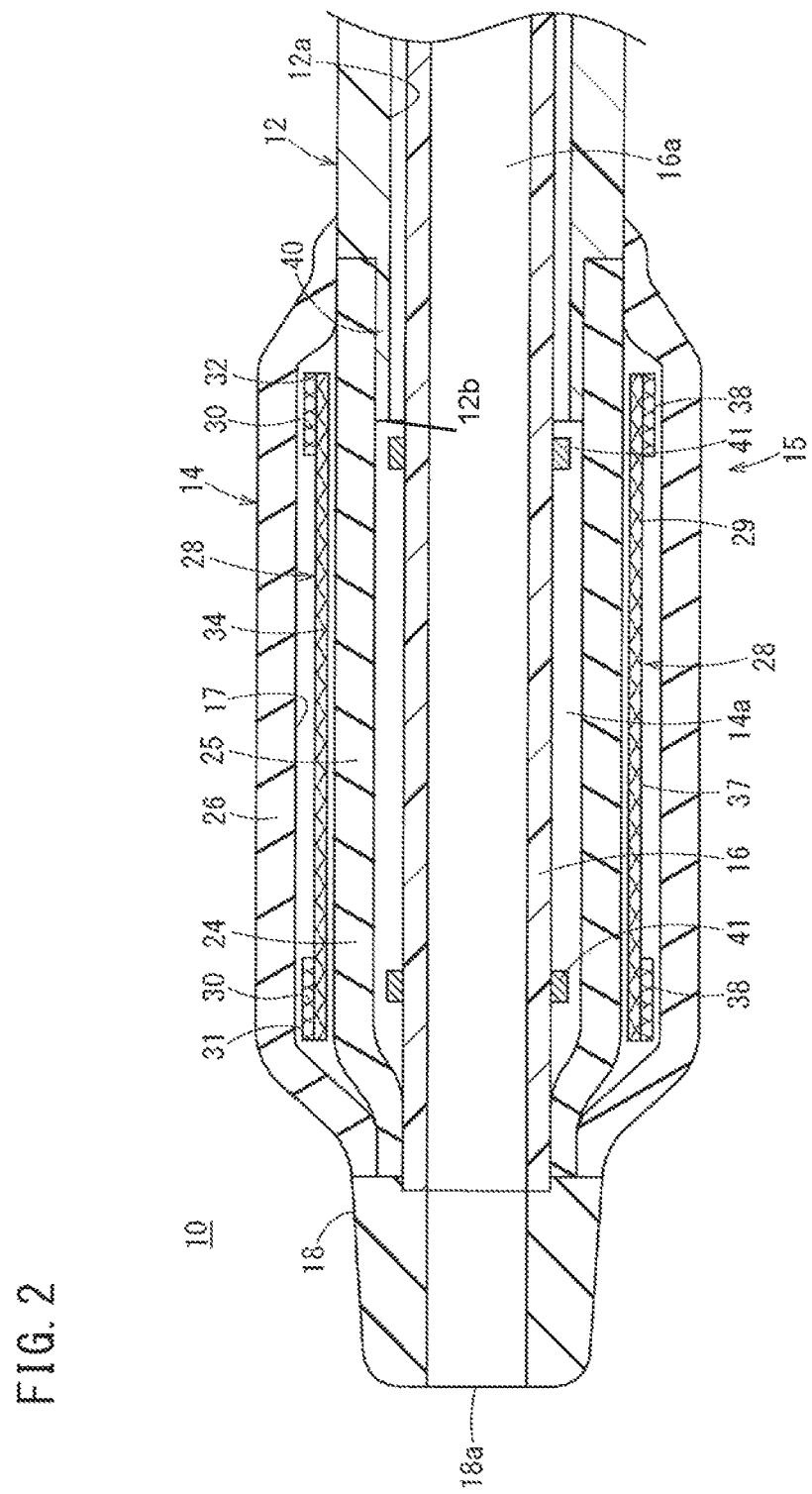
FIG. 2 is a schematic cross-sectional view of the distal portion of the catheter illustrated in FIG. 1.

As illustrated in FIG. 1 and FIG. 2, the catheter 10 includes the long shaft 12 having a small diameter, the balloon 14 joined to the distal end of the shaft 12, a reinforcement member 28 disposed inside a membrane (wall) forming the balloon 14, an inner tube 16 inserted through the shaft 12 and the balloon 14, a distal tip 18 joined to the distal end of the balloon 14, and a hub 20 provided on the proximal side of the shaft 12.

In FIG. 1, the catheter 10 is configured as a so-called "rapid exchange-type" catheter provided with an opening portion 22 through which a guide wire 21 is guided out, in a middle portion of the shaft 12 in a longitudinal direction. In another embodiment, the catheter 10 may be configured as an "over-the-wire-type" catheter in which a guide wire lumen is formed throughout the overall length of the catheter 10, and the guide wire 21 is guided out from the proximal end of the hub 20.

The shaft 12 is a flexible tube of which both ends in an axial direction are open, and which is long and has a small diameter. The shaft 12 extends from the rear end of the balloon 14 to the distal end of the hub 20. A portion from the distal end to the opening portion 22 configures a double tube which forms an inflation lumen 12a between the shaft 12 and the inner tube 16, and a portion from the opening portion 22 to the hub 20 is a single tube. The shaft 12 forms the inflation lumen 12a through which an inflation fluid for the balloon 14 is supplied.

In the shaft 12, the inflation fluid is pressure-fed from a pressure applying apparatus such as an indeflator (not illustrated) connected via a luer taper 20a or the like provided in the hub 20 to the balloon 14. For example, the inflation fluid is a contrast agent, a physiological salt solution, or a mixture thereof.

The inner tube 16 is a guide wire tube forming a wire lumen 16a through which the guide wire 21 is inserted. The distal end of the inner tube 16 is positioned on the distal side beyond the proximal end of the distal tip 18. The inner tube 16 extends inside the balloon 14 and the shaft 12, and the proximal end thereof is liquid-tightly joined to the opening portion 22 (refer to FIG. 1) formed in an intermediate portion of the shaft 12. Therefore, the guide wire 21, which has been inserted through a distal end opening portion 18a serving as an entrance at the distal tip 18, is inserted through the wire lumen 16a of the inner tube 16 from the distal side toward the proximal side and is guided out through the opening portion 22 serving as an exit.

It is favorable to provide a radiopaque marker 41 on the inner tube 16 inside the balloon 14. The radiopaque marker 41 is configured with an X-ray opaque (radiopaque) material (for example, gold, platinum, tungsten, or a mixture thereof). The radiopaque marker 41 is used for visually recognizing the position of the balloon 14 in a living body under an X-ray contrast condition. For example, the radiopaque marker 41 can be configured to have a tubular shape (ring shape). Note that, as in exemplary FIG. 2, multiple radiopaque markers 41 may be provided on the inner tube 16 inside the balloon 14 while being spaced from each other in the axial direction. Alternatively, only one radiopaque marker 41 may be provided on the inner tube 16 inside the balloon 14.

It is preferable that the shaft 12 and the inner tube 16 have structures with appropriate flexibility and appropriate rigidity such that an operator can smoothly insert the long catheter 10 into a biological organ such as a blood vessel while grasping and operating the proximal side of the catheter 10. Therefore, for example, it is preferred that the shaft 12 and the inner tube 16 are formed of a polymeric material such as polyolefin (for example, polyethylene, polypropylene, polybutene, an ethylene-propylene copolymer, an ethylene-vinyl acetate copolymer, ionomer, and a mixture of two or more types thereof), polyvinyl chloride, polyamide, a polyamide elastomer, polyurethane, a polyurethane elastomer, polyimide, and a fluorine resin, or a mixture thereof; or a multi-layer tube including two or more types thereof.

The balloon 14 can be inflated and dilated in response to a change of internal pressure. The distal portion of the balloon 14 is joined to a portion in the vicinity of the distal portion of the inner tube 16, and the proximal portion of the balloon 14 is joined to the distal portion of the shaft 12. An internal space 14a of the balloon 14 communicates with the inflation lumen 12a.

Via the inflation lumen 12a, the inflation fluid can flow into (be guided into) the balloon 14 and the inflation fluid can be discharged from the balloon 14. In response to the inflation fluid guided into the balloon 14, the balloon 14 is inflated in a radial direction. As indicated with the imaginary line in FIG. 1, when the balloon 14 is maximally inflated, a portion between the distal end and the proximal end exhibits a shape which is increased in diameter and has a substantially uniform outer diameter along the axial direction.

The balloon 14 is required to have appropriate flexibility so as to be able to pass through a meandering or bending portion of a body lumen. In addition, the balloon 14 is required to have strength to the extent that a lesion can be reliably widened, and the balloon 14 is also required to have high-pressure resistance and low compliance properties. Therefore, in the exemplary embodiment, the balloon 14 has an inner layer 24 and an outer layer 26 having tubular shapes, having elastic stretching properties, and forming the fluid-impermeable balloon walls. The reinforcement member 28 is disposed between the inner layer 24 and the outer layer 26. The balloon 14 and the reinforcement member 28 define a dilation portion 15 which can be inflated and deflated in the radial direction at the distal portion of the catheter 10.

The inner layer 24 transfers force to the reinforcement member 28 in response to the inflation fluid being guided into the balloon 14 (pressurization), and the inner layer 24 expands to an extent, but the shape thereof is restricted along the inflated shape of the reinforcement member 28. The outer layer 26 expands along the inflation shape of the reinforcement member 28 in response to the dilation fluid guided into the balloon 14 (pressurization), and the outer layer 26 contracts to the extent of the initial shape in response to the inflation fluid discharged from the inside of the balloon 14 (decompression) in order to restore the original shape (position) of the reinforcement member 28. Therefore, it is preferable that the outer layer 26 is formed of a base material having a high stretching recovery rate.

The inner layer 24 and the outer layer 26 are joined to each other at the distal portions and the proximal portions, for example, through fusing or bonding. An annularly sealed accommodation chamber 17 accommodating the reinforcement member 28 is formed between the inner layer 24 and the outer layer 26.

Examples of the materials of the inner layer 24 and the outer layer 26 include various types of rubber material such as natural rubber, butyl rubber, isoprene rubber, butadiene rubber, styrene-butadiene rubber, and silicone rubber; various types of thermoplastic elastomer such as a polyurethane-based elastomer, a polyester-based elastomer, a polyamide-based elastomer, an olefin-based elastomer, and a styrene-based elastomer; mixtures thereof; and the like. The material of the inner layer 24 and the material of the outer layer 26 may be the same as each other or may be different from each other.

The reinforcement member 28 is a tubular net-shaped member which is disposed between the inner layer 24 and the outer layer 26 such that at least a part thereof is movable with respect to the balloon 14, and the reinforcement member 28 functions to enhance pressure resistance of the balloon 14.

The reinforcement member 28 has both end portions (first end portion 31 and second end portion 32) in the axial direction, and an intermediate portion 34 defining the middle between the first end portion 31 and the second end portion 32. In the reinforcement member 28, at least one of the first end portion 31 and the second end portion 32, and the intermediate portion 34 are not fixed to the inner layer 24 and the outer layer 26. Accordingly, movement with respect to the inner layer 24 and the outer layer 26 in the axial direction and a circumferential direction is allowed.

In addition, the inner layer 24 and the outer layer 26 may be fixedly attached (for example, fused or bonded) via a gap (mesh) between threads 29 and/or a gap between threads 30 forming the reinforcement member 28. Accordingly, while the reinforcement member 28 is allowed to move with respect to the inner layer 24 and the outer layer 26 to a certain extent, the movement range of the reinforcement member 28 can be restricted.

In a case of the exemplary embodiment, the other one of the first end portion 31 or the second end portion 32 is also not fixed to the inner layer 24 and the outer layer 26. Accordingly, movement with respect to the inner layer 24 and the outer layer 26 in the axial direction is allowed. In other words, in the exemplary embodiment, the reinforcement member 28 is not fixed to any one of the inner layer 24 and the outer layer 26. Therefore, the reinforcement member 28 can freely move in the circumferential direction and the axial direction within a range restricted by the inner layer 24 and the outer layer 26 (within a range of the accommodation chamber 17).

Note that, only one of the first end portion 31 or the second end portion 32 may be fixed to the inner layer 24 or the outer layer 26. In this case, fixing means is not limited to any particular means and suitable fixing means such as fusing and bonding may be employed.

In addition, the reinforcement member 28 has a first sleeve 37, and second sleeves 38 which respectively surround both the end portions of the first sleeve 37 in the axial direction. A maximally inflated diameter D2 of the second sleeve 38 is set so as to be smaller than a maximally inflated diameter D1 of the first sleeve 37 (refer to FIG. 3B).

The first sleeve 37 includes a tubular net-shaped body formed by knitting (weaving) one or more threads 29, and the first sleeve 37 has stretching properties in at least the circumferential direction (and the radial direction). The second sleeve 38 includes a tubular net-shaped body formed by knitting (weaving) one or more threads 30, and the second sleeve 38 has stretching properties in at least the circumferential direction (and the radial direction). The axial-directional length of the second sleeve 38 is less than half the axial-directional length of the first sleeve 37. For example, the axial-directional length of the second sleeve 38 ranges approximately from 10% to 30% of the axial-directional length of the first sleeve 37 and preferably ranges approximately from 10% to 20%.

Figure 3A:
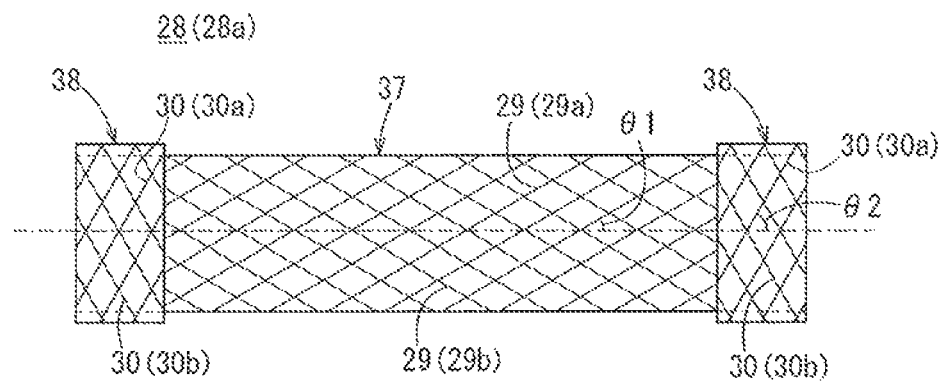
FIG. 3A is a side view illustrating a reinforcement member when being deflated.
Figure 3B:
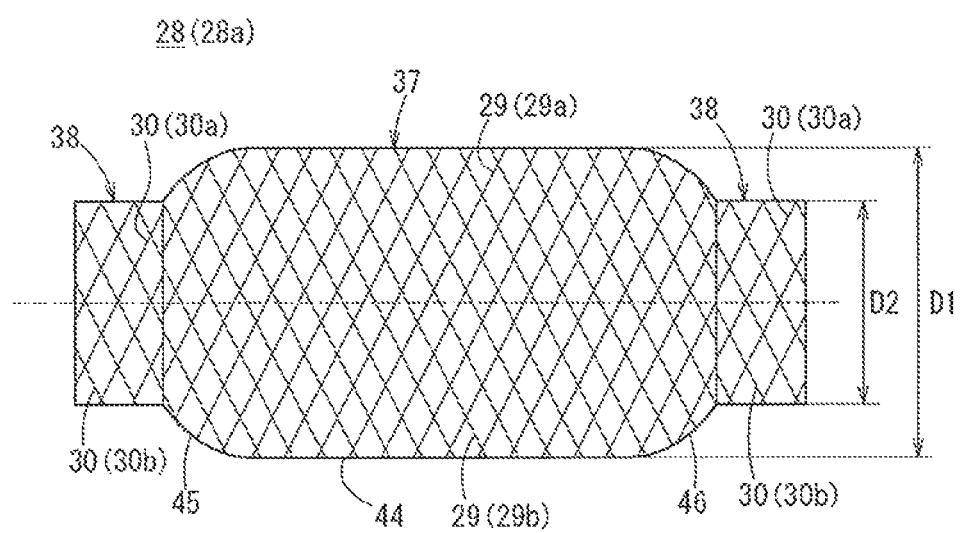
FIG. 3B is a side view illustrating the reinforcement member when being inflated.

FIG. 3A is a side view illustrating the reinforcement member 28 when being deflated, and FIG. 3B is a side view illustrating the reinforcement member 28 when being inflated. As illustrated in FIG. 3B, when the balloon 14 is inflated, in the reinforcement member 28, both the end portions of the first sleeve 37 are inflated up to only the maximally inflated diameter D2 of the second sleeve 38, and other portions of the first sleeve 37 (intermediate portion 34) are inflated in the radial direction so as to be greater than the second sleeve 38.

In this case, the shape of the reinforcement member 28 (intermediate portion 34) when inflated includes a straight portion 44 having a substantially uniform outer shape, and outer-diameter varying portions (tapered portions) 45 and 46 which are respectively positioned on both sides of the straight portion 44 and are decreased in diameter outward in the axial direction. Note that, in a case where the balloon 14 is produced by using the reinforcement member 28 described in FIGS. 3A and 3B, the balloon 14 when inflated includes a straight portion having a substantially uniform outer shape due to the reinforcement member 28, and outer-diameter varying portions (tapered portions) which are respectively positioned on both sides of the straight portion and are decreased in diameter outward in the axial direction. In such a case, the radiopaque marker 41 is disposed on the inner tube 16 such that the position of the straight portion of the balloon 14 can be confirmed. Accordingly, since an operator can visually recognize the position having the maximally inflated diameter in the balloon 14 under an X-ray contrast condition, positioning between the region of the maximally inflated diameter in the balloon 14, and the lesion can be easily performed.

For example, the ratio of the maximally inflated diameter D2 of the second sleeve 38 to the maximally inflated diameter D1 of the first sleeve 37 is set to range from 20% to 70% and, more preferably, from 30% to 40%.

The method of forming the first sleeve 37 and the second sleeve 38 is not limited to any particular form. Examples of the method include braiding and tube-knitting. As in FIGS. 3A and 3B, in a case of a reinforcement member 28a in which the first sleeve 37 and the second sleeve 38 are formed through braiding, in the first sleeve 37, multiple threads 29 (one or more threads 29a extending in a first spiral direction and one or more threads 29b extending in a second spiral direction) are woven so as to intersect each other, thereby forming the tubular net-shaped body. In addition, in the second sleeve 38, multiple threads 30 (one or more threads 30a extending in the first spiral direction and one or more threads 30b extending in the second spiral direction) are woven so as to intersect each other, thereby forming the tubular net-shaped body.

In the reinforcement member 28a illustrated in FIGS. 3A and 3B, since a weaving angle θ2 of the thread 30 configuring the second sleeve 38 is greater than a weaving angle θ1 of the thread 29 configuring the first sleeve 37, the maximally inflated diameter D2 of the second sleeve 38 is set so as to be smaller than the maximally inflated diameter D1 of the first sleeve 37. The weaving angle is an inclination angle of the thread 29 or the thread 30 with respect to the axial direction of the first sleeve 37 or the second sleeve 38 in the initial state (deflated state).

In a case of the reinforcement member 28a illustrated in FIGS. 3A and 3B, depending on the method of weaving the first sleeve 37 (for example, the threads 29a and the threads 29b are mutually woven one by one or are mutually woven two by two) or the weaving pitch of the threads 29 (disposition space between the threads 29a or the threads 29b in the axial direction), the flexibility and the strength of the reinforcement member 28a can be adjusted.

When the balloon 14 is inflated, as in FIG. 3B, the threads 29 and 30 respectively configuring the first sleeve 37 and the second sleeve 38 are displaced to the critical angle. In this case, due to the difference between the weaving angles 81 and 82 of the threads 29 and 30 in the first sleeve 37 and the second sleeve 38, the inflating amount of the second sleeve 38 is smaller than the inflating amount of the first sleeve 37. Therefore, both end portions of the first sleeve 37 that are surrounded by the second sleeves 38 are restrained by the second sleeves 38 from inflating in the radial direction.

Figure 4A:
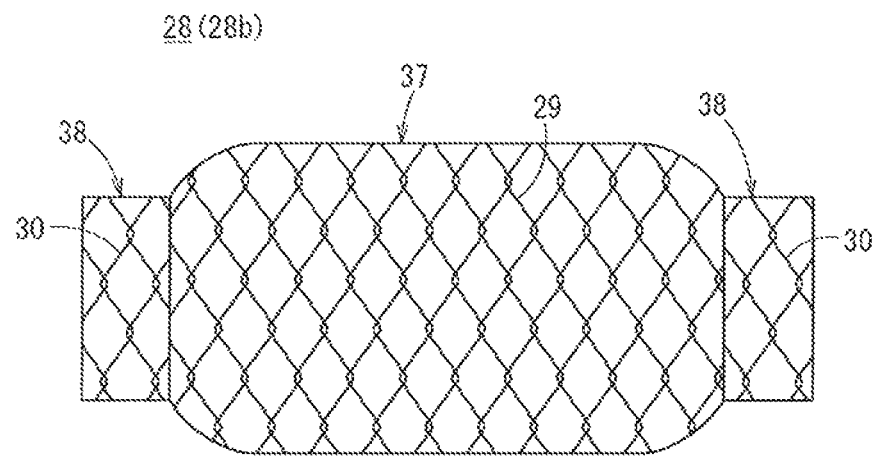
FIG. 4A is a side view illustrating a reinforcement member in another configuration example.

Referring also to FIG. 4A, in a case of a reinforcement member 28b in which the first sleeve 37 and the second sleeve 38 are formed through tube-knitting, in the first sleeve 37, the threads 29 extending in the circumferential direction in a waved manner are arranged in the axial direction, and the waved threads 29 adjacent to each other in the axial direction are interlaced with each other. In addition, in the second sleeve 38, the threads 30 extending in the circumferential direction in a waved manner are arranged in the axial direction, and the waved threads 30 adjacent to each other in the axial direction are interlaced with each other.

In the case of the reinforcement member 28b, when being compressed in the circumferential direction, the threads 29 and 30 are folded. Accordingly, the reinforcement member 28b is decreased in diameter. In addition, when the reinforcement member 28b is compressed in the axial direction, the threads 29 and 30 of the meshes are misaligned and the threads 29 and the threads 30 respectively adjacent to each other in the axial direction can overlap each other. Moreover, the reinforcement member 28b can be bent in accordance with rotations of the interlaced portions between the threads 29 and the threads 30 respectively adjacent to each other in the axial direction. Therefore, such a reinforcement member 28b has excellent flexibility with respect to bending.

With respect to the reinforcement member 28b illustrated in FIG. 4A, even in a case where the first sleeve 37 and the second sleeve 38 are formed through tube-knitting, the amount of deformation of each of the sleeves 37 and 38 in the circumferential direction is adjusted based on the loop length and the number of loops of the threads 29 and 30. Accordingly, the maximally inflated diameter D2 of the second sleeve 38 can be set so as to be smaller than the maximally inflated diameter D1 of the first sleeve 37.

Figure 4B:
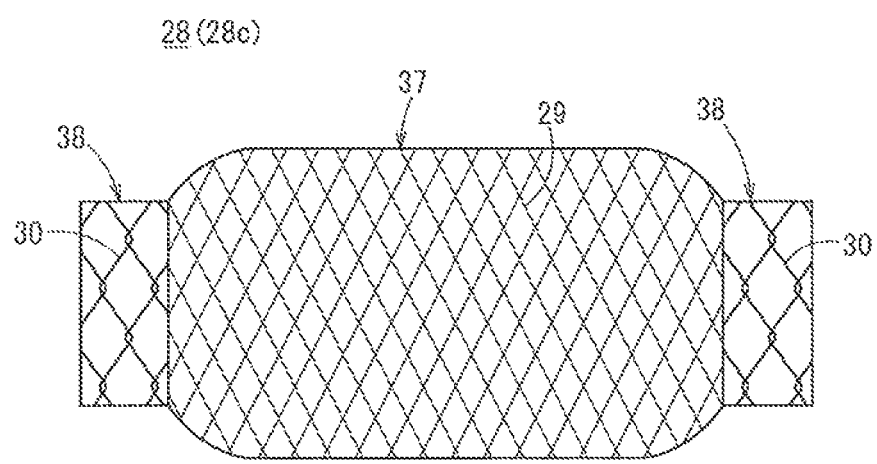
FIG. 4B is a side view illustrating a reinforcement member in a further configuration example.

The method of knitting the first sleeve 37 and the method of knitting the second sleeve 38 are not necessarily the same as each other. The methods thereof may be different from each other. Even in this case, when the method of knitting each of the sleeves 37 and 38 is adjusted, the maximally inflated diameter D2 of the second sleeve 38 can be set so as to be smaller than the maximally inflated diameter D1 of the first sleeve 37. Therefore, for example, as in a reinforcement member 28c illustrated in FIG. 4B, the first sleeve 37 may be formed through braiding, and the second sleeve 38 may be formed through tube-knitting. Or alternatively, the first sleeve 37 may be formed through tube-knitting, and the second sleeve 38 may be formed through braiding (not illustrated).

Note that, the first sleeve 37 and the second sleeve 38 are not limited to the above-described knitting method and may be formed through a different knitting method.

In order to apply high-pressure resistance and low compliance properties to the balloon 14, as the threads 29 and 30 configuring the reinforcement member 28, it is preferable to employ threads having high strength and a high elastic modulus, for example, twisted threads formed of high-strength fibers (super fibers) of which the tensile break strength is equal to or greater than 2 GPa and an elastic modulus is equal to or greater than 50 GPa. Examples of such high-strength fibers include an aramid fiber, a carbon fiber, a polyarylate fiber, a PBO fiber, ultra-high molecular weight polyethylene, and an LCP fiber.

For example, the diameters of the threads 29 and 30 may range approximately from 5 to 100 μm. In a case where twisted threads formed of the high-strength fibers is used as the threads 29 and 30, for example, a single fiber diameter of the high-strength fiber may range approximately from 5 to 30 μm. As the high-strength fiber, for example, a fiber having a single fiber diameter of 12 μm can be used. However, a thinner fiber may be used, and a thicker fiber may be used. In a case of a thicker fiber, it is favorable to employ a loosely twisted thread so as to be in an unraveled state when tensile force is not applied to the twisted thread.

The threads 29 configuring the first sleeve 37 and the threads 30 configuring the second sleeve 38 may be threads of the same type or may be threads of a different type.

It is preferable that the friction coefficient on the surface of the threads 30 (fibers) configuring the second sleeve 38 is significant such that the friction coefficient of the second sleeve 38 with respect to the outer layer 26 becomes greater than the friction coefficient of the first sleeve 37 with respect to the outer layer 26. Accordingly, the reinforcement member 28 can be restrained from causing significant positional misalignment between the inner layer 24 and the outer layer 26 of the balloon 14 in the axial direction from the initial position. In addition, when the frictional resistance between the outer surface of the first sleeve 37 and the inner surface of the second sleeve 38 is increased, the second sleeve 38 can more effectively conduct a function of restricting inflation of both the end portions of the first sleeve 37.

In this case, for example, when the surface roughness of the threads 30 configuring the second sleeve 38 is caused to be greater than the surface roughness of the threads 29 configuring the first sleeve 37, the friction coefficient of the second sleeve 38 with respect to the outer layer 26 can be greater than the friction coefficient of the first sleeve 37 with respect to the outer layer 26.

As illustrated in FIG. 2, the distal portion of the inner layer 24 is joined to the inner tube 16. In addition, the proximal portion of the inner layer 24 is joined to the distal portion (thin portion 40) of the shaft 12, and the outermost distal portion 12b of the shaft 12 is positioned on the distal side beyond the innermost proximal portion of the inner layer 24, on the inner side of the inner layer 24. Therefore, a stretchable region (hereinafter, will be referred to as "stretchable region 25 of the inner layer 24") in the inner layer 24 during deformation of inflation and deflation of the balloon 14 is a portion between a joint spot of the inner layer 24 and the inner tube 16, and the outermost distal portion 12b of the shaft 12.

The innermost proximal portion of the reinforcement member 28 is positioned on the proximal side beyond the innermost proximal portion of the stretchable region 25 in the inner layer 24.

In FIGS. 1 and 2, the distal tip 18 provided on the distal side of the balloon 14 is a portion which flexibly advances through a curved portion, an irregular portion, and the like inside a biological organ, as the outermost distal end of the catheter 10, penetrates a lesion (stenosed portion), and leads the catheter 10 to be smoothly inserted through. The distal tip 18 is a short tube having an inner diameter substantially the same as the inner diameter of the inner tube 16.

The distal tip 18 is fitted to the distal portion of the inner tube 16 from the outside so as to be liquid-tightly joined to the distal portion of the inner tube 16. The distal tip 18 protrudes toward the distal side beyond the distal end opening portion of the wire lumen 16a, and the proximal surface thereof is joined to the distal surface of the balloon 14. The distal end opening portion 18a of the distal tip 18 communicates with the wire lumen 16a of the inner tube 16 and serves as the entrance of the guide wire 21.

The material and the shape of the distal tip 18 are suitably set such that the distal tip 18 is configured to be more flexible than at least the shaft 12 and the inner tube 16. Note that, the distal tip 18 may be omitted. In such a case, it is preferred to employ a configuration in which the outermost distal end position of the inner tube 16 and the outermost distal end position of the balloon 14 coincide with each other, or a configuration in which the outermost distal end position of the inner tube 16 slightly protrudes beyond the outermost distal end position of the balloon 14.

An example of a method of manufacturing the catheter 10 (mainly, a step of manufacturing the inflation portion 15 and peripheral portions thereof) will be described below. Note that, the disclosure here is not limited to the exemplified manufacturing method. In FIGS. 5A to 11B, the tubular net-shaped reinforcement member 28 is schematically illustrated, and the reinforcement member 28 is not limited to any particular knitting method.

Figure 5A:
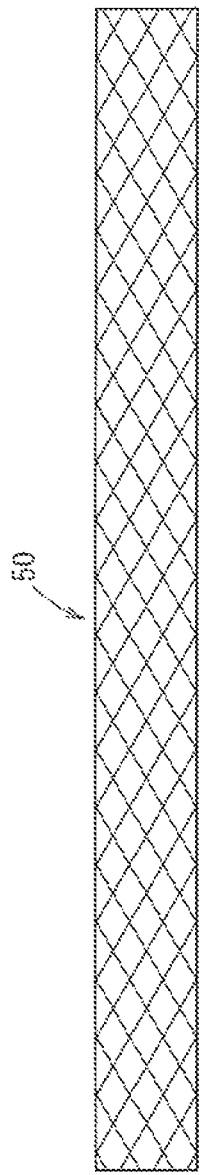
FIG. 5A is a view describing a step of preparing a first base material sleeve.
Figure 5B:
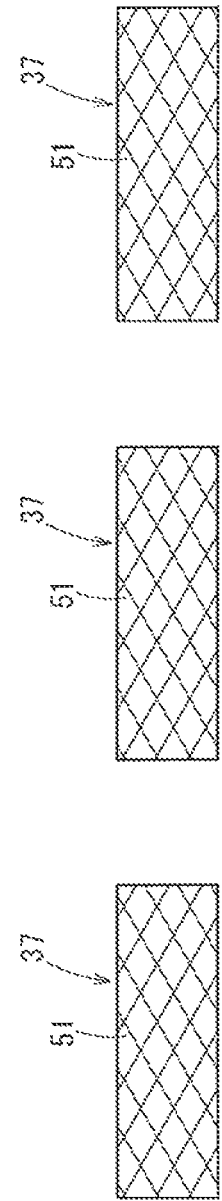
FIG. 5B is a view describing a step of obtaining multiple first sleeves from the first base material sleeve.

FIGS. 5A and 5B are views describing a step of manufacturing the first sleeve 37. Referring to FIG. 5A, first, a step of preparing a tubular net-shaped first base material sleeve 50 which becomes the base material of the first sleeve 37 (step of preparing a base material sleeve) is executed. The first base material sleeve 50 has a length equal to or greater than that of multiple first sleeves 37. In this case, for example, the first base material sleeve 50 is formed by knitting the above-described high-strength fibers so as to have a tubular net shape. Subsequently, as in FIG. 5B, the first base material sleeve 50 is cut at one or more locations in the axial direction, thereby obtaining multiple first sleeves 37 having desired lengths (first cutting step).

Figure 6A:
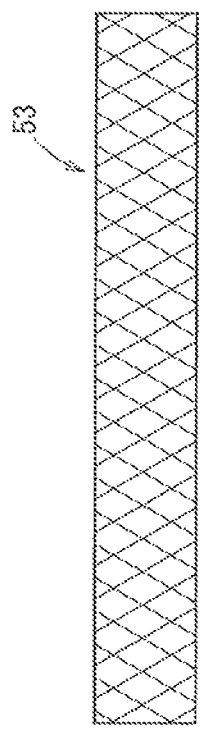
FIG. 6A is a view describing a step of preparing a second base material sleeve.
Figure 6B:
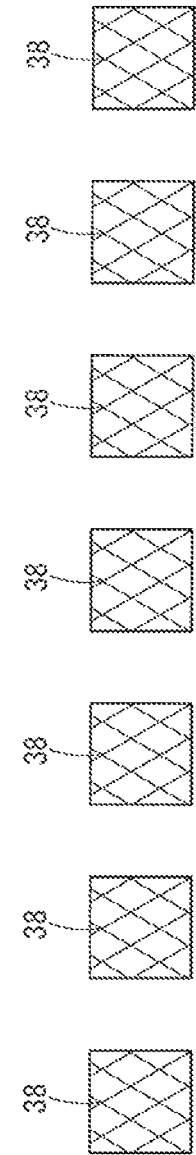
FIG. 6B is a view describing a step of obtaining multiple second sleeves from the second base material sleeve.

FIGS. 6A and 6B are views describing a step of manufacturing the second sleeve 38. Referring to FIG. 6A, first, a step of preparing a tubular net-shaped second base material sleeve 53 which becomes the base material of the second sleeve 38 (step of preparing a base material sleeve) is executed. The second base material sleeve 53 has a length equal to or greater than that of multiple second sleeves 38. In this case, for example, the second base material sleeve 53 is formed by knitting the above-described high-strength fibers so as to have a tubular net shape. Subsequently, as in FIG. 6B, the second base material sleeve 53 is cut at one or more locations in the axial direction, thereby obtaining multiple second sleeves 38 having desired lengths (second cutting step).

Figure 7A:
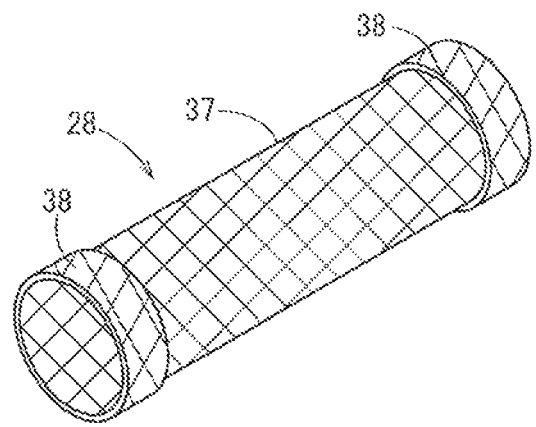
FIG. 7A is a view describing a step of covering both end portions of the first sleeve with the second sleeves.

Subsequently, as in FIG. 7A, a positioning step in which both the end portions of the first sleeve 37 are covered with the second sleeves 38 (step of covering a sleeve) is executed. Accordingly, it is possible to obtain the reinforcement member 28 in which both the end portions of the first sleeve 37 are surrounded by the second sleeves 38. Note that, in the reinforcement member 28, the first sleeve 37 and the second sleeve 38 are not bonded or fused to each other, thereby not being fixed to each other.

Figure 7B:
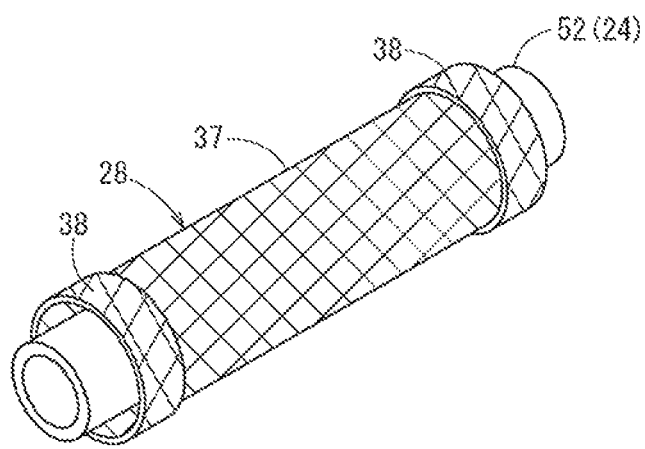
FIG. 7B is a view describing a step of covering an inner layer with the reinforcement member.

Subsequently, as in FIG. 7B, a step of covering an inner layer tube 52 which is the base material of the inner layer 24, with the reinforcement member 28 (step of covering a reinforcement member) is executed. In this case, both end portions of the inner layer tube 52 respectively protrude beyond openings at both ends of the reinforcement member 28.

Figure 7C:
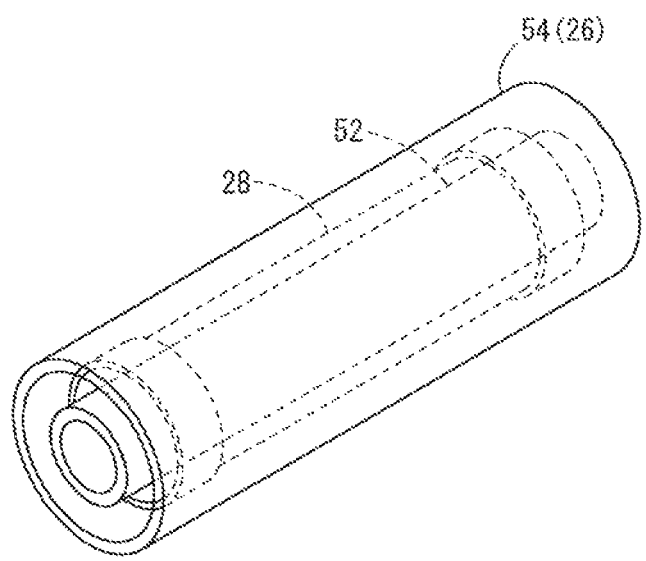
FIG. 7C is a view describing a step of covering the inner layer and the reinforcement member with an outer layer.
Figure 8A:
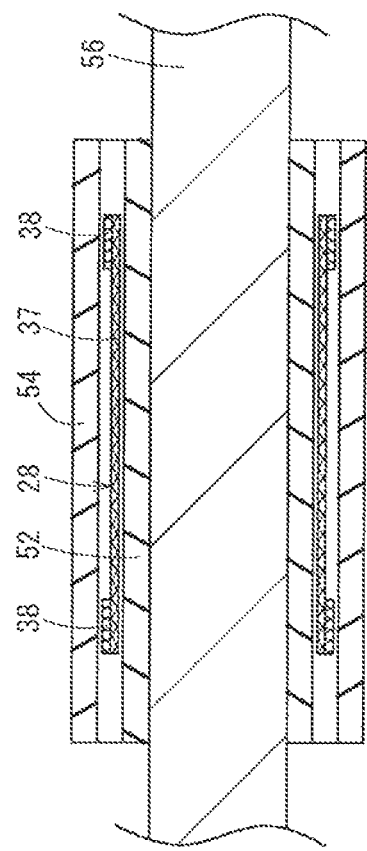
FIG. 8A is a first view describing a step of joining the inner layer and the outer layer to each other.
Figure 8B:
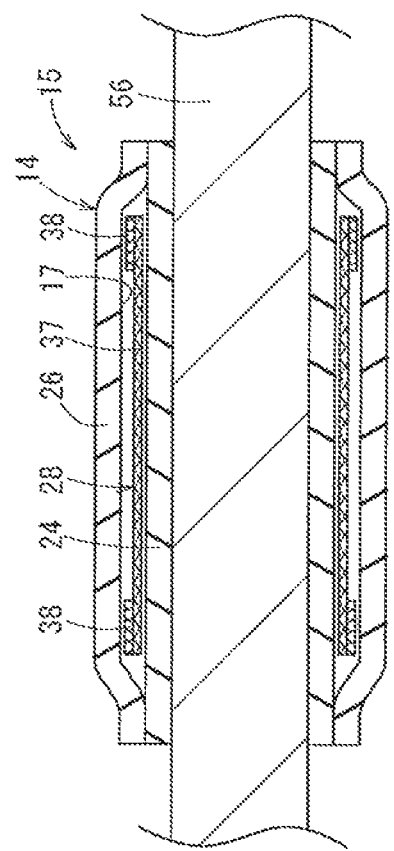
FIG. 8B is a second view further describing the step of joining the inner layer and the outer layer to each other.

Subsequently, as in FIG. 7C, a step of covering the inner layer tube 52 and the reinforcement member 28 (reinforcement member 28 in a state where the inner layer tube 52 is inserted into the inner side) with an outer layer tube 54 which is the base material of the outer layer 26 (step of covering an outer layer) is executed. In this case, the inner layer tube 52 and the reinforcement member 28 are covered with the outer layer tube 54 such that the overall length of the reinforcement member 28 is housed inside the outer layer tube 54 (both end portions of the outer layer 26 protrude in the axial direction beyond both end portions of the reinforcement member 28).

Subsequently, a step of joining the inner layer tube 52 and the outer layer tube 54 (step of joining inner and outer layers) is executed. Specifically, first, as in FIG. 8A, a mandrel 56 (core bar) is inserted into the inner layer tube 52 (assembly of the inner layer tube 52, the outer layer tube 54, and the reinforcement member 28). Subsequently, as in FIG. 8B, the inner layer tube 52 and the outer layer tube 54 are fused so as to be joined to each other at one end portion and the other end portion. Accordingly, the annularly sealed accommodation chamber 17 is formed between the inner layer 24 and the outer layer 26, thereby obtaining the inflation portion 15 in a state where the reinforcement member 28 is disposed inside the accommodation chamber 17. After the step of joining inner and outer layers, the mandrel 56 is removed.

In this case, in the exemplary embodiment, the reinforcement member 28 is merely disposed inside the accommodation chamber 17 and is not joined to other members through fusing, bonding, or the like. Therefore, the reinforcement member 28 is not fixed to any portion of the balloon 14 (inner layer 24 and outer layer 26).

Subsequently, a step of joining the balloon 14 (inflation portion 15) and the shaft 12 to each other (step of joining a balloon and a shaft) is executed (FIGS. 9A and 9B). Specifically, the thin portion 40 is formed at the distal portion of the shaft 12. In this case, for example, the distal portion of the shaft 12 is drawn down (the mandrel is inserted into a hollow portion of the shaft 12, and the distal portion of the shaft 12 is pressedly input into a mold which includes a hole having a diameter smaller than that of the shaft 12), and thus, the distal portion can have a reduced diameter. In FIG. 9A, the thin portion 40 of the shaft 12 is inserted into the proximal side of the balloon 14. Subsequently, as in FIG. 9B, the proximal portion of the balloon 14 and the distal portion (thin portion 40) of the shaft 12 are fused so as to be joined to each other.

Subsequently, even though the step is not illustrated, the radiopaque marker 41 is attached to the inner tube 16. Specifically, the tubular radiopaque marker 41 having an inner diameter slightly greater than the inner tube 16 is caused to pass through the outer side of the inner tube 16, and the mandrel is inserted into the inner tube 16. Thereafter, the entire circumference of the radiopaque marker 41 is hammered (swaging step). The radiopaque marker 41 is decreased in diameter and is engaged with the inner tube 16. In this manner, the radiopaque marker 41 is fixed to the inner tube 16.

Subsequently, a step of joining the balloon 14 and the inner tube 16 to each other (step of joining a balloon and an inner tube) is executed (FIGS. 10A and 10B). Specifically, as in FIG. 10A, the inner tube 16 is inserted into the balloon 14 and the shaft 12. Subsequently, as in FIG. 10B, the distal portion of the balloon 14 and the inner tube 16 are fused so as to be joined to each other.

Subsequently, a step of joining the distal tip 18 and the inner tube 16 to each other (step of joining a distal tip and an inner tube) is executed (FIGS. 11A and 11B). Specifically, first, the distal portion of the inner tube 16 is cut, and the length is adjusted (FIG. 11A). Subsequently, the proximal portion of the distal tip 18 is fitted to the distal portion of the inner tube 16 from the outside, and the proximal portion of the distal tip 18 and the distal portion of the inner tube 16 are fused so as to be joined to each other (FIG. 11B).

Note that, a step of joining the proximal end of the shaft 12 and the distal portion of the hub 20 to each other (step of joining a shaft and a hub) can be executed at an arbitrary time. For example, the step of joining a shaft and a hub may be executed before the step of joining a balloon and a shaft, may be executed after the step of joining a distal tip and an inner tube, or may be executed between the step of joining a balloon and a shaft and the step of joining a distal tip and an inner tube.

In the above-described manufacturing method, as the means for joining members to each other, fusing is exemplified. However, instead of fusing, other types of joining means such as bonding or the like may be applied.

The catheter 10 according to the exemplary embodiment is basically configured as described above. Hereinafter, operations and effects thereof will be described.

For example, treatment using the catheter 10 is performed as follows. First, a form of a lesion (stenosed portion) occurring inside a blood vessel is identified through an intravascular contrast method or an intravascular ultrasound diagnosis method. Subsequently, for example, the guide wire 21 is percutaneously guided into a blood vessel in advance through a Seldinger's method, and the guide wire 21 is inserted through the wire lumen 16a of the inner tube 16 from the distal end opening portion 18a of the distal tip 18. While the guide wire 21 is guided out through the opening portion 22, the catheter 10 is inserted into a blood vessel. Under a radioscopic condition, the guide wire 21 is caused to advance toward a target lesion. The guide wire 21 is caused to pass through the lesion and to indwell, and the catheter 10 is caused to advance along the guide wire 21.

When the distal tip 18 of the catheter 10 passes through the lesion, the balloon 14 is positioned at the lesion. When the inflation fluid (for example, contrast agent) is pressure-fed into the inflation lumen 12a from the hub 20 side, the balloon 14 is inflated and the lesion is widened. Accordingly, treatment of the lesion can be performed. Subsequently, the inflation fluid is suctioned from the inside of the balloon 14 to the hub 20 side through the inflation lumen 12a, and the balloon 14 is deflated again. In a case where an additional lesion required to be treated is present at a different portion inside a body lumen, the balloon 14 is delivered to the additional lesion, the balloon 14 is inflated and deflated in a similar manner as described above. When the procedure for all of the lesions in a treatment object is completed, the catheter 10 is removed from the body.

In the catheter 10 according to the exemplary embodiment as described above, due to the reinforcement member 28, high-pressure resistance and low compliance properties can be applied to the balloon 14. In addition, since the reinforcement member 28 has a degree of freedom for moving with respect to the balloon 14, favorable flexibility of the balloon 14 can be maintained. Accordingly, it is possible to realize the balloon 14 having high crossability even inside a complicatedly meandering body lumen.

Particularly, in a case of the exemplary embodiment, in the reinforcement member 28, at least one of the first end portion 31 or the second end portion 32, and the intermediate portion 34 are not directly fixed to the balloon 14. Here, the expression "at least one of the first end portion 31 or the second end portion 32, and the intermediate portion 34 are not directly fixed to the inner layer 24 and the outer layer 26" denotes that at least one of the first end portion 31 or the second end portion 32, and the intermediate portion 34 are not bonded to the inner layer 24 and the outer layer 26 and are not embedded in the inner layer 24 and the outer layer 26, thereby being able to freely move inside a space formed between the inner layer 24 and the outer layer 26. In other words, substantially the entirety of the reinforcement member 28 has a degree of freedom for moving in the axial direction and the circumferential direction with respect to the balloon 14. Therefore, favorable flexibility of the balloon 14 can be maintained. Accordingly, it is possible to realize the balloon 14 having high crossability inside a body lumen.

Moreover, in a case of the exemplary embodiment, not only one of the first end portion 31 or the second end portion 32 but also the other one thereof is not fixed to any one of the inner layer 24 and the outer layer 26. According to the configuration, the reinforcement member 28 is not fixed to any portion in the balloon 14. Therefore, the degree of freedom for moving the reinforcement member 28 with respect to the balloon 14 can be further improved, and flexibility can be improved. In accordance therewith, crossability inside a body lumen can be further improved.

Figure 12:
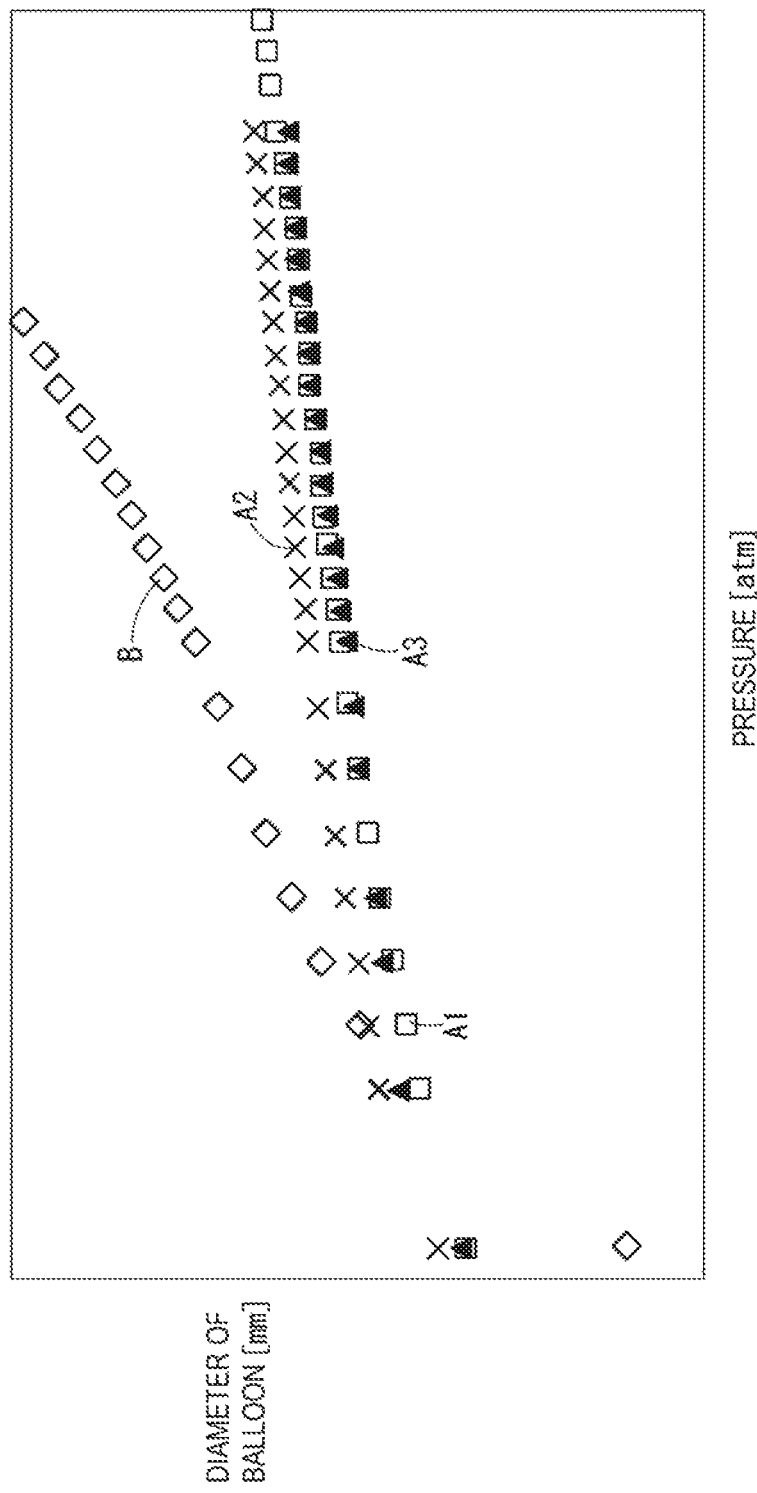
FIG. 12 is a graph illustrating a relationship between pressure and a balloon diameter regarding balloons in which forms of fixing the reinforcement member are different from each other, and a balloon provided with no reinforcement member.

Referring to FIG. 12, a relationship is graphically illustrated between pressure and a balloon diameter regarding balloons A1 to A3 which are provided with the reinforcement member 28 and in which forms of fixing the reinforcement member 28 are different from each other, and a balloon B provided with no reinforcement member 28. In FIG. 12, in the balloon A1, both the end portions of the reinforcement member 28 in the axial direction are fixed to the inner layer 24. In the balloon A2, only one end portion of the reinforcement member 28 in the axial direction is fixed to the inner layer 24. In the balloon A3, the reinforcement member 28 is not fixed to any portion.

According to FIG. 12, it is found that in the balloons A1 to A3 provided with the reinforcement member 28, compared to the balloon B provided with no reinforcement member 28, the increase of the balloon diameter with respect to the increase of the pressures is gentle (modest), while having high pressure resistance and low compliance properties. Meanwhile, in the balloons A1 to A3 provided with the reinforcement member 28, no meaningful difference based on the forms of fixing the reinforcement member 28 is recognized. Therefore, it is understood that the balloon 14 having high-pressure resistance and low compliance properties can be realized by providing the reinforcement member 28 between the inner layer 24 and the outer layer 26, regardless of whether or not the reinforcement member 28 is fixed. Therefore, from the viewpoint of maintaining favorable flexibility of the balloon 14 and improving crossability of the catheter 10 inside a body lumen, it is preferred that at least one between both the end portions of the reinforcement member 28, and the intermediate portion 34 are not fixed to the inner layer 24 and the outer layer 26 of the balloon 14.

In a case of the exemplary embodiment, the reinforcement member 28 has the first sleeve 37, and the second sleeves 38 which respectively surround both the end portions of the first sleeve 37 in the axial direction. The maximally inflated diameter D2 of the second sleeve 38 is set so as to be smaller than the maximally inflated diameter D1 of the first sleeve 37. Accordingly, when the balloon 14 is inflated, in the reinforcement member 28, both the end portions of the first sleeve 37 are inflated up to only the maximally inflated diameter D2 of the second sleeve 38, and other portions of the first sleeve 37 (intermediate portion 34) are inflated so as to be greater than the second sleeve 38. Thus, inside a body lumen, the balloon 14 can be inflated so as to have a desired shape, and a procedure can be effectively performed with respect to a lesion.

In a case of the exemplary embodiment, the friction coefficient of the second sleeve 38 with respect to the outer layer 26 is greater than the friction coefficient of the first sleeve 37 with respect to the outer layer 26. With this configuration, the reinforcement member 28 can be restrained from causing significant positional misalignment between the inner layer 24 and the outer layer 26 of the balloon 14 in the axial direction from the initial position. In addition, when the friction coefficient between the first sleeve 37 and the second sleeve 38 is increased, the degree of freedom of mutual movement between the first sleeve 37 and the second sleeve 38 is degraded. Therefore, the second sleeve 38 can more effectively conduct a function of restricting inflation.

In addition, as in FIGS. 3A and 3B, in a case where the first sleeve 37 and the second sleeve 38 are formed through braiding, when the weaving angle θ2 of the threads 30 configuring the second sleeve 38 is greater than the weaving angle θ1 of the threads 29 configuring the first sleeve 37, it is possible to simply establish a configuration in which the maximally inflated diameter D2 of the second sleeve 38 is smaller than the maximally inflated diameter D1 of the first sleeve 37.

In a case of the exemplary embodiment, the balloon 14 is inflated and deflated while entailing elastic stretching and is a zero folding-type balloon which is not folded when being in a deflated state. Accordingly, the balloon can easily restore the original outer diameter when being deflated again after inflation. Therefore, in a case where multiple lesions occur in locations different from each other inside a body lumen and are treated with the same balloon 14, the outer diameter after being deflated again is restrained from becoming greater than the initial outer diameter. Therefore, even after the balloon 14 is deflated again, favorable crossability inside a body lumen can be maintained.

Furthermore, the balloon 14 having elastic stretching properties can be prepared without performing blow molding. Therefore, the catheter 10 can be conveniently manufactured. In other words, in a case of a balloon which is configured with a non-stretchable material, the balloon is required to be molded so as to have a desired shape by executing blow molding after manufacturing the base material of the balloon. Moreover, in order to cause the balloon to be in a deflated state, there is a need to execute a wrapping step in which the balloon is folded (one or more outer circumferential portions of the balloon are folded in the circumferential direction in an overlapping manner). In contrast, in a case of the balloon 14 of the exemplary embodiment, as it is clear from the above-described manufacturing method, blow molding is not necessary and the wrapping step thereafter is also not necessary. Therefore, it is possible to reduce the number of steps and to lower the manufacturing cost.

In a case of the exemplary embodiment, the reinforcement member 28 is formed of high-strength fibers of which tensile break strength is equal to or greater than 2 GPa and an elastic modulus is equal to or greater than 50 GPa. According to the configuration, it is possible to realize the balloon 14 having excellent high-pressure resistance and low compliance properties.

The detailed description above describes a catheter and a method of manufacturing a catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
a balloon that has an inner layer and an outer layer having elastic stretching properties, having tubular shapes, and being able to be inflated and deflated in response to a change of internal pressure; and
a tubular net-shaped reinforcement member disposed between the inner layer and the outer layer such that at least a part thereof is movable with respect to the balloon,
wherein the reinforcement member has a first sleeve, and at least two second sleeves which respectively surround each end portion of the first sleeve in an axial direction,
wherein the first sleeve and the at least two second sleeves are configured such that a maximally inflated diameter of the at least two second sleeves is smaller than a maximally inflated diameter of the first sleeve.

2. The catheter according to claim 1,
wherein a friction coefficient of the at least two second sleeves with respect to the inner layer or the outer layer is greater than a friction coefficient of the first sleeve with respect to the inner layer or the outer layer.

3. The catheter according to claim 1,
wherein each of the first sleeve and the at least two second sleeves is formed by weaving a plurality of wire members together in an intersecting manner, and
wherein a weaving angle of the plurality of wire members configuring the second sleeve is greater than a weaving angle of the plurality of wire members configuring the first sleeve, whereby the maximally inflated diameter of the second sleeve is configured to be smaller than the maximally inflated diameter of the first sleeve.

4. The catheter according to claim 1,
wherein the reinforcement member is formed of high-strength fibers of which tensile break strength is equal to or greater than 2 GPa and an elastic modulus is equal to or greater than 50 GPa.

5. A balloon configured to be inflated and deflated for use with an inflation catheter, the balloon comprising:
an inner layer and an outer layer, the inner layer and the outer layer being joined together at a distal portion and a proximal portion to thereby form an accommodation chamber;
a reinforcement member disposed between the inner layer and the outer layer and confined within the accommodation chamber;
wherein the reinforcement member includes a first end portion, a second end portion, and an intermediate portion;
wherein at least one of the first end portion, the second end portion and the intermediate portion is not fixed to the inner layer and said at least one of the first end portion, the second end portion and the intermediate portion is also not fixed to the outer layer.

6. The balloon according to claim 5,
wherein the reinforcement member comprises a first sleeve and at least two second sleeves, one of the at least two second sleeves surrounding the first end portion of the first sleeve and another one of the at least two second sleeves surrounding the second end portion of the first sleeve.

7. The balloon according to claim 6,
wherein the first sleeve defines a first maximally inflated diameter and each of the second sleeves define a second maximally inflated diameter, the second maximally inflated diameter being smaller than the first maximally inflated diameter.

8. The balloon according to claim 7,
wherein a ratio of the second maximally inflated diameter to the first maximally inflated diameter is 20% to 70%.

9. The balloon according to claim 6,
wherein an axial direction length of each of the at least two second sleeves is less than half of an axial directional length of the first sleeve.

10. The balloon according to claim 6,
wherein the first sleeve includes a tubular body formed by weaving a plurality of first members together in an intersecting manner;
wherein each of the at least two second sleeves includes a tubular body formed by weaving a plurality of second members together in an intersecting manner;
wherein a weaving angle of the plurality of second members forming each of the at least two second sleeves is greater than a weaver angle of the plurality of first members forming the first sleeve.

11. The balloon according to claim 10,
wherein a friction coefficient of the at least two second sleeves with respect to the inner layer or the outer layer is greater than a friction coefficient of the first sleeve with respect to the inner layer or the outer layer.

12. The balloon according to claim 5,
wherein the reinforcement member is formed of high-strength fibers of which tensile break strength is equal to or greater than 2 GPa and an elastic modulus is equal to or greater than 50 GPa.

13. The balloon according to claim 5,
wherein, when the balloon is inflated, the intermediate portion of the reinforcement member includes a straight portion, and the first end portion and the second end portion include tapered portions.

14. A catheter comprising:
an elongated shaft;
an inner tube; and
the balloon according to claim 5 disposed on a distal end of the elongated shaft, the inner tube extending through the shaft and the balloon.

* * * * *